US011699962B2

(12) United States Patent
Wang et al.

(10) Patent No.: US 11,699,962 B2
(45) Date of Patent: Jul. 11, 2023

(54) CONTINUOUS BIOMECHANICAL ENERGY HARVESTER FROM BREATH-ASSOCIATED TORSO MOVEMENT

(71) Applicant: The Regents of the University of California, Oakland, CA (US)

(72) Inventors: Yun Wang, Irvine, CA (US); Guohao Liu, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 960 days.

(21) Appl. No.: 16/580,854

(22) Filed: Sep. 24, 2019

(65) Prior Publication Data

US 2020/0099319 A1    Mar. 26, 2020

Related U.S. Application Data

(60) Provisional application No. 62/735,425, filed on Sep. 24, 2018.

(51) Int. Cl.
*H02N 11/00*       (2006.01)
*H02K 35/00*       (2006.01)
(Continued)

(52) U.S. Cl.
CPC .......... *H02N 11/002* (2013.01); *A61B 5/082* (2013.01); *A61B 5/0816* (2013.01); *H02K 7/06* (2013.01);
(Continued)

(58) Field of Classification Search
CPC ......... H02N 11/00; H02N 11/002; A45F 5/02; A45F 5/021; A61B 5/0816; A61B 5/082;
(Continued)

(56) References Cited

U.S. PATENT DOCUMENTS

2,029,148 A * 1/1936 Archer ................. H02K 7/1853
310/75 B
3,268,845 A * 8/1966 Whitmore ............ A61B 5/1135
600/534
(Continued)

*Primary Examiner* — Burton S Mullins
(74) *Attorney, Agent, or Firm* — Nguyen Tarbet LLC (57) ABSTRACT

A system, device and method are provided for continuously generating more than 0.01 watt of electrical energy by harnessing mechanical or kinetic energy from a reciprocating motion of a user's torso during breathing. The reciprocating motion causes reciprocating lateral and medial translation of two chambers of the device housing. That reciprocating lateral and medial translation rotates a gear, which in turn, drives a dynamo to produce electrical energy. Since the conversion from the mechanical energy of the spinning rod to power is direct, the energy-conversion efficiency may be up to 90% or higher. The device may further comprise one or more charging means for providing electrical energy to one or more peripheral electronic devices. In some embodiments, additional integrated functions may include auxiliary energy storage, backup energy, emergency power, mini-MP3 player, data recorder, GPS interface, miniature video recorder, speaker, abdomen muscle exercise, timing, Bluetooth interface, and heath information analyzer.

11 Claims, 8 Drawing Sheets

(51) Int. Cl.
    *H02K 7/18*         (2006.01)
    *A61B 5/08*         (2006.01)
    *H02K 7/116*       (2006.01)
    *H02K 11/00*       (2016.01)
    *H02K 7/06*         (2006.01)

(52) U.S. Cl.
    CPC ......... *H02K 7/116* (2013.01); *H02K 11/0094* (2013.01)

(58) Field of Classification Search
    CPC ........ A61H 2002/12; A61H 2201/1207; A61H 2201/1253; H02K 7/06; H02K 7/116; H02K 11/0094; H02K 7/1853
    USPC .......................................................... 290/1 R
    See application file for complete search history.

(56) References Cited

U.S. PATENT DOCUMENTS

| | | | | |
|---|---|---|---|---|
| 4,245,640 | A * | 1/1981 | Hunt | H02K 7/1876 607/33 |
| 5,358,461 | A * | 10/1994 | Bailey, Jr. | A63B 21/153 290/1 R |
| 7,345,372 | B2 * | 3/2008 | Roberts | H02P 9/006 310/309 |
| 7,361,999 | B2 * | 4/2008 | Yeh | H02K 7/1853 290/1 R |
| 7,638,889 | B2 * | 12/2009 | Yeh | H02K 7/1853 290/1 R |
| 9,190,886 | B2 * | 11/2015 | Stanton | F03G 5/06 |
| 9,362,803 | B2 * | 6/2016 | Panousis | H02J 7/34 |
| 10,263,494 | B2 * | 4/2019 | Spencer | H02J 7/345 |
| 10,454,297 | B2 * | 10/2019 | Zhang | H02J 50/70 |
| 10,491,003 | B2 * | 11/2019 | Amin | H02M 3/1588 |

\* cited by examiner

CONTINUOUS BIOMECHANICAL ENERGY HARVESTER FROM BREATH-ASSOCIATED TORSO MOVEMENT

CROSS-REFERENCES TO RELATED APPLICATIONS

This application is a non-provisional and claims the benefit of U.S. Provisional Patent Application No. 62/735,425, filed Sep. 24, 2018 the specification of which is incorporated herein in its entirety by reference.

GOVERNMENT SUPPORT

This invention was made with Government support under Grant No. CBET-1336873, awarded by the National Science Foundation. The Government has certain rights in the invention.

FIELD OF THE INVENTION

The present invention generally relates to the generation of electrical energy using mechanical energy harnessed from a breath-associated, reciprocate motion of a human torso 200, as well as integrated functions 212 powered by such motion.

BACKGROUND OF THE INVENTION

Harvesting the human body's energy for conversion to power reaching 0.01 watt or higher is challenging. Efforts have been attempted using thermoelectric devices, which seek to generate power via human body heat. These devices face very low efficiency (typically less than 10%) and low electrical output (typical ranges are in the order of micro- and milli-watts) in power generation. Moreover, the efficiency of thermoelectric devices is limited by the Canot cycle, which is determined by the highest temperature in the heat reservoir. For the typical body temperature of 37° C. and the standard environment temperature of about 20° C., the Canot efficiency is approximately 17K/300K—6%. This makes the production of 0.01 watt power from torso heat difficult. Some efforts are made to utilize the movement of other human bodies for energy conversion, including hands, arms, and legs, which cannot provide continuous power (i.e., 24 hours, 7 days a week).

The present invention proposes utilizing the mechanical energy generated by the breath-associated movement of a human's torso 200 (e.g., the abdomen and chest) to continuously generate power. This power is efficient and potentially enables the achievement of 0.01 watt or higher electrical output. Since the torso movement is continuous (i.e., 24 hours, 7 days a week), the invention can continuously supply electrical energy to electronic devices, e.g., cell phones and portable electric devices.

The housing 100 of the present invention may be disposed on the ventral face of a garment 101 such that the continuous expansion and retraction of the torso 200 of a person (due to breathing) produces mechanical energy that the housing directs upon the rotation of a gear. The gear's rotation drives a dynamo 308, which produces electrical energy that may be stored for later provision to peripheral devices. Since the conversion from the kinetic energy of the spinning rod to power is direct, the energy-conversion efficiency may be 90% or higher.

Additionally, the person wearing the article may choose to utilize the device for the exercise of abdominal muscles. To further this intended use, the device may further comprise a display providing a measure of generated electrical energy (or possibly caloric expenditure) to, the person. This way, the person may increase or decrease abdomen muscle movement to achieve a desired level of power generation. Additionally, the continuous power generation offers opportunities to integrate other functions 212 including, but not limited to, mini MP3 or video players, data recorders, GPS interfaces, Bluetooth interfaces, implant devices, and health analyzers.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention provides a system, device, and method for continuously generating electrical energy using mechanical or kinetic energy harnessed from the reciprocating motion of a user's torso 200 during breathing. A garment 101 may be disposed on the torso 200 of the user such that reciprocating, transverse expansion and retraction of the torso 200 causes reciprocating lateral and medial translation of two chambers (306 and 307) of the device housing 100. That reciprocating lateral and medial translation may rotate a gear 306, which in turn, may drive a dynamo 308 to produce electrical energy. In some embodiments, the device may comprise: a housing 100 further comprising two chambers (306 and 307) coupled to each other to allow only one degree of translational freedom; a gear 305 operatively coupled to the housing 100, such that reciprocating medial and lateral translation of the chambers rotates the gear 305; a dynamo 308 configured to convert mechanical or kinetic energy received from the spinning gear 306 to electrical energy; and a means (operatively coupled to the dynamo 308) of storing electrical energy. The device may additionally comprise an electrical output interface 209 (operatively coupled to the energy storage means 207) for controlling a provision of electrical energy to one or more electronic devices via one or more charging means 304, including (but not limited to) USB ports, Firewire ports (having 6 pins), HDMI ports, MHL ports, 3.5 mm jacks, etc. In some embodiments, the power generation may provide power for other integrated functions 212 including, but not limited to, mini-MP3 or video players, data recorders, GPS interfaces, Bluetooth interfaces, implant devices, and health analyzers. In some embodiments, the device may be an exercise controller for breath-associated muscles.

In exemplary embodiments, the garment 101 may be a belt 213 or a harness 214. The reciprocating motion of the user's torso 200 comprises a transverse expansion and retraction of the torso 200. Belt clamps (409 and 410) (bilaterally disposed on both sides of the device) may secure the device to the belt 213 of harness 214.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE INVENTION

The following description sets forth numerous specific details (e.g., specific configurations, parameters, examples, etc.) of the disclosed embodiments, examples of which are illustrated in the accompanying drawings. It should be recognized, however, that such description is not intended as a limitation on the scope of the disclosed embodiments, but is intended to elaborate upon the description of these embodiments. It will be evident to a person of ordinary skill in the art that the present invention can be practiced without every specific detail described infra. Moreover, well-known methods, procedures, components, and circuits have not been described in detail so as not to unnecessarily obscure aspects of the embodiments of the invention.

It is fully contemplated that the features, components, and/or steps described with respect to one embodiment may be combined with the features, components, and/or steps described with respect to other embodiments of the present disclosure. To avoid needless descriptive repetition, one or more components or actions described in accordance with one exemplary embodiment can be used or omitted as applicable from other embodiments. For the sake of brevity, the numerous iterations of these combinations will not be described separately. The same reference numbers may be used to refer to the same or similar elements in different drawings. Alternately, different reference numbers may be used to refer to the same or similar elements in the drawings of different embodiments. Any distinction of an element's reference number in one embodiment from another is not limiting in any way, does not suggest that elements of one embodiment could not be combined with or substituted for elements in another embodiment, and (most importantly) is specifically intended only to facilitate the matching of elements in the disclosure to their corresponding claim recitations.

Where two or more elements are said to be "coupled," the meaning shall include (in addition to configurations where the elements directly operate with each other because they are joined) configurations where the elements indirectly operate with each other (e.g., through one or more intermediate elements) so long as there is a link.

It will be appreciated that the term "ventral" is used herein with reference to the ventral surface of the torso 200 specifically (e.g., the chest and the abdomen), which is a subset of the total set of ventral surfaces of the body that are known in the art (e.g., the chest, abdomen, shins, palms, and soles). The term "transverse" is used herein with reference to any plane passing through a torso 200 that is parallel to the transverse plane (known also in the art as the axial/horizontal plane), which divides the body into superior and inferior parts (where the terms "superior" and "inferior" are used as known in the art). When the term "medial" is used to describe a direction, the term is used as it is known in the art to refer to movements, forces, vectors, or trajectories directed toward the mid-sagittal plane. When the term "medial" is used to describe a position relative to a point of reference, the position of the medial element is either on the mid-sagittal plane or between the mid-sagittal plane and the point of reference. The term "lateral" is used as it is known in the art to refer to movements, forces, vectors, or trajectories directed away from the mid-sagittal plane.

When used herein, terms describing direction (such as, but not limited to, "medial," "lateral", "expansion," and "contraction"), position (such as, but not limited to, "ventral") and orientation (such as, but not limited to, "transverse") are not limiting upon the claims unless expressly recited therein.

Figure 1A:
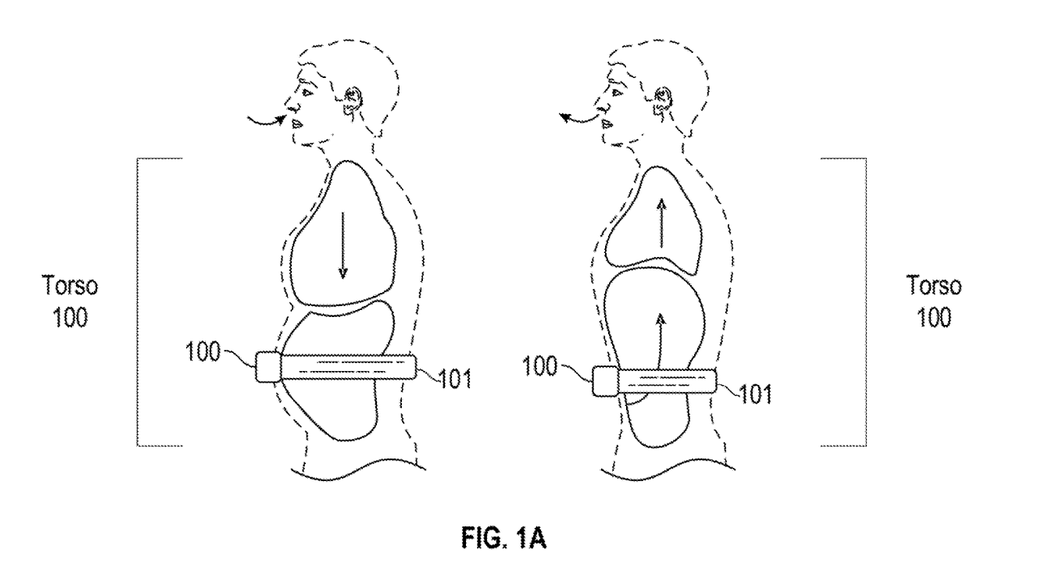
FIG. 1A illustrates a representation of the installation of the device of the present invention and power generated during abdomen movement.
Figure 1B:
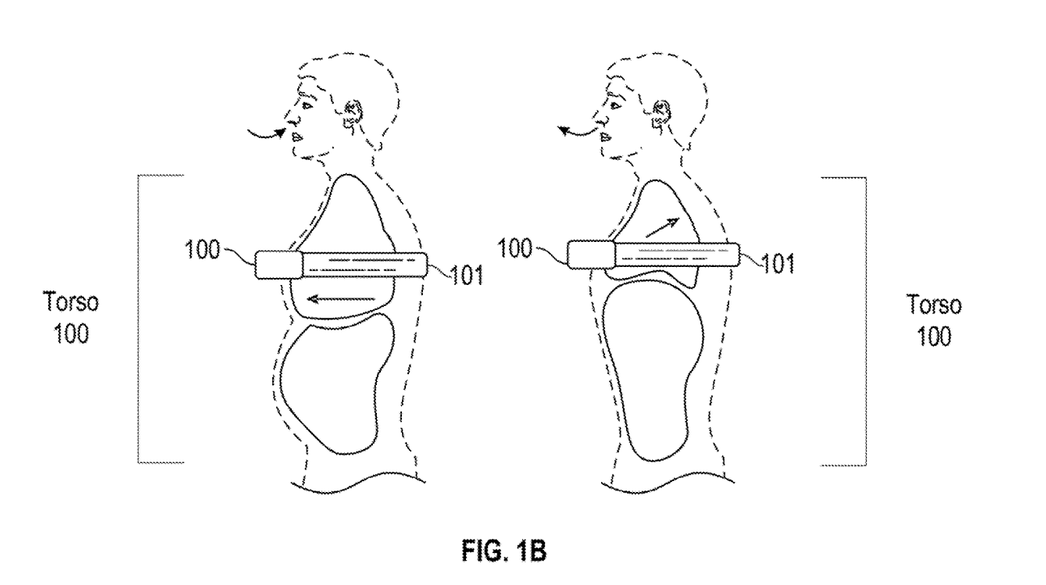
FIG. 1B illustrates a representation of the installation of the device of the present invention and power generated during chest movement.
Figure 2:
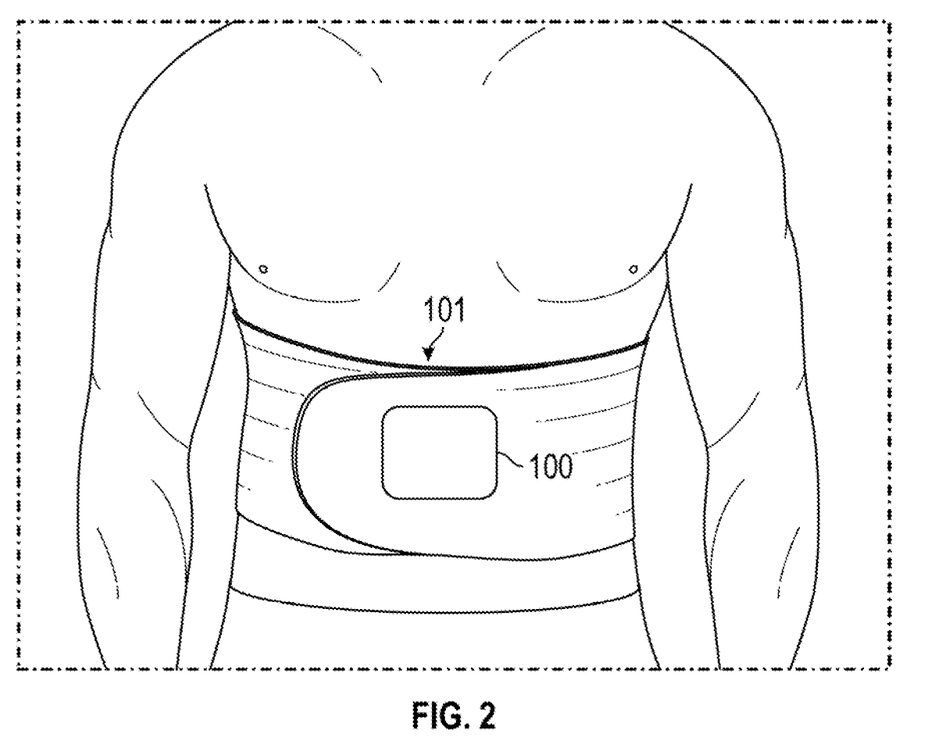
FIG. 2 illustrates the device of the present invention coupled to an article worn by a user.
Figure 3:
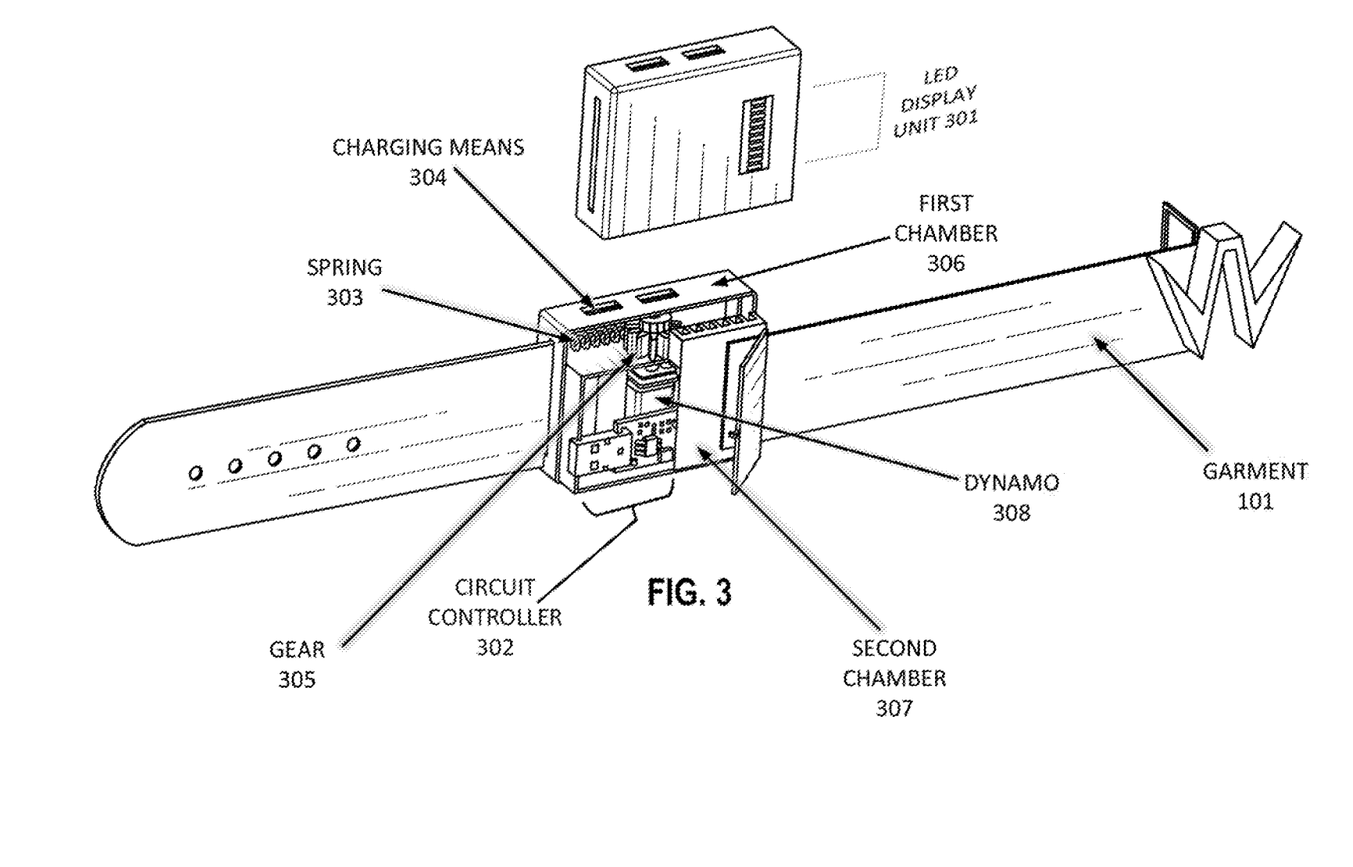
FIG. 3 illustrates device components comprising an embodiment of the present invention.
Figure 7:
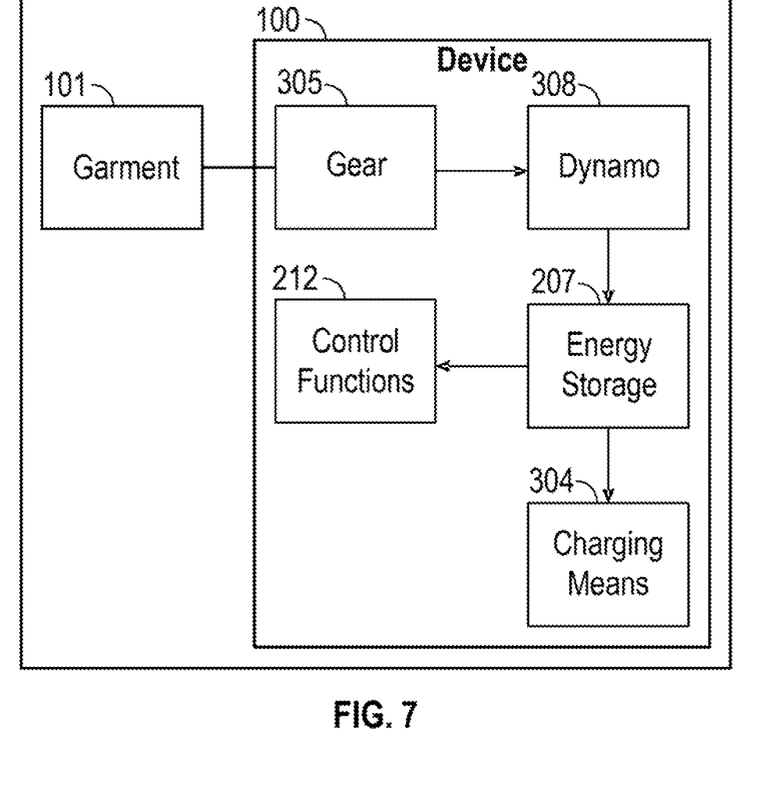
FIG. 7 shows a simplified block diagram of the present device including auxiliary energy storage and integrated functions 212.
Figure 8:
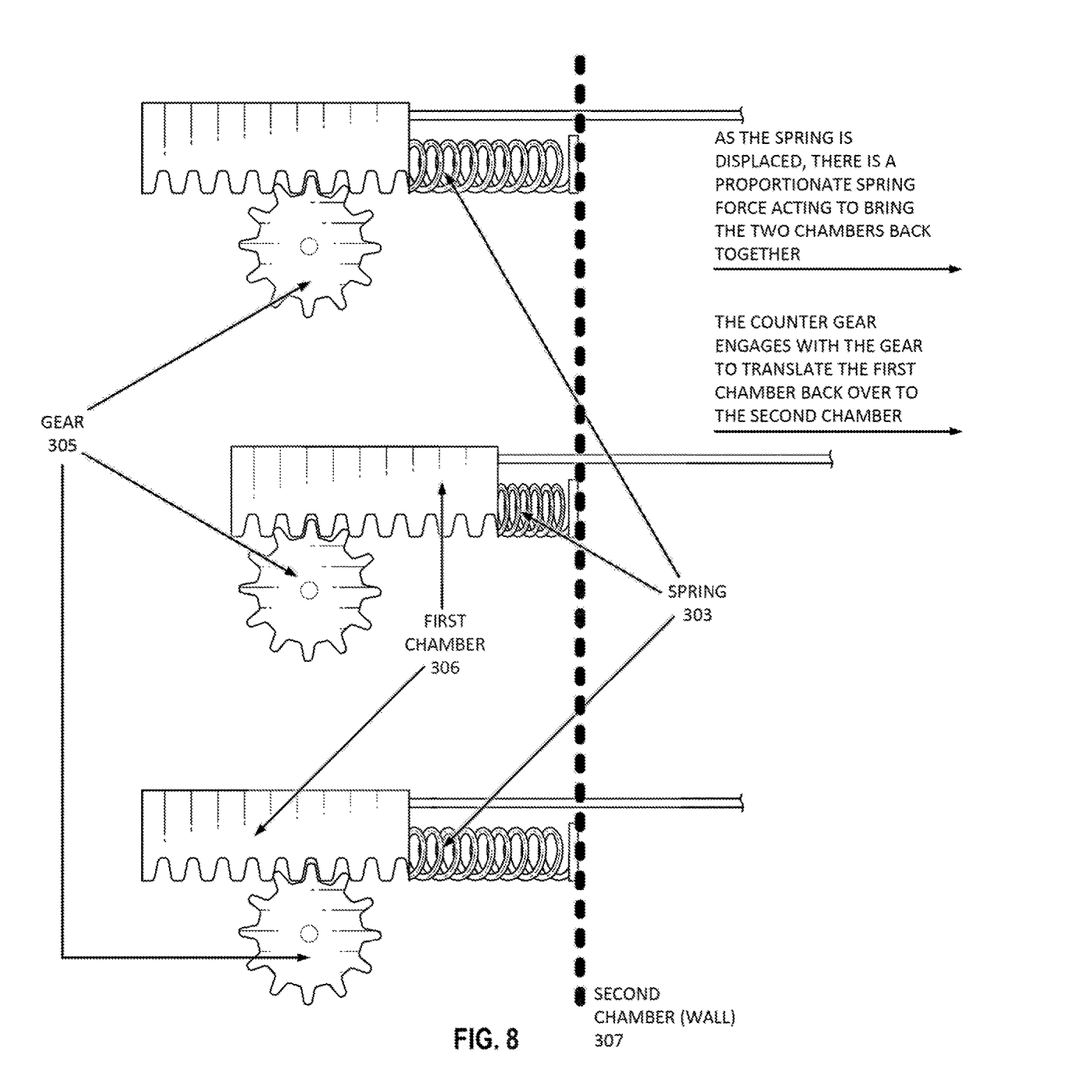
FIG. 8 diagrams a non-limiting exemplary configuration of one embodiment of the present invention where the first chamber 306 is coupled to one end of the spring 303 and the other end of spring 303 is coupled to the second chamber 307.

FIG. 1 diagrams how a breathing motion transversely expands and retracts the torso 200, which then expands and retracts the garment 101 (shown, by way of non-limiting example, as a belt 213 or a harness 214). FIG. 7 shows a simplified block diagram of the present device including auxiliary energy storage and integrated functions 212. FIG. 2 illustrates, by way of non-limiting example, one embodiment of the present invention. FIG. 3 illustrates, by way of non-limiting example, another exemplary embodiment of the present invention.

Figure 5A:
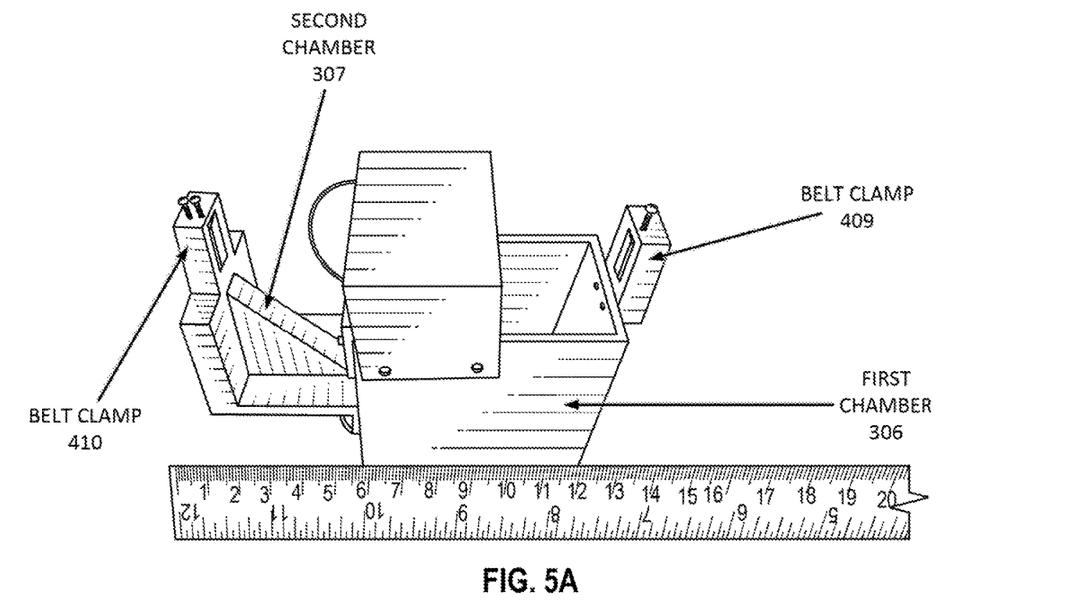
FIG. 5A shows a prototype of the device of the present invention.
Figure 5B:
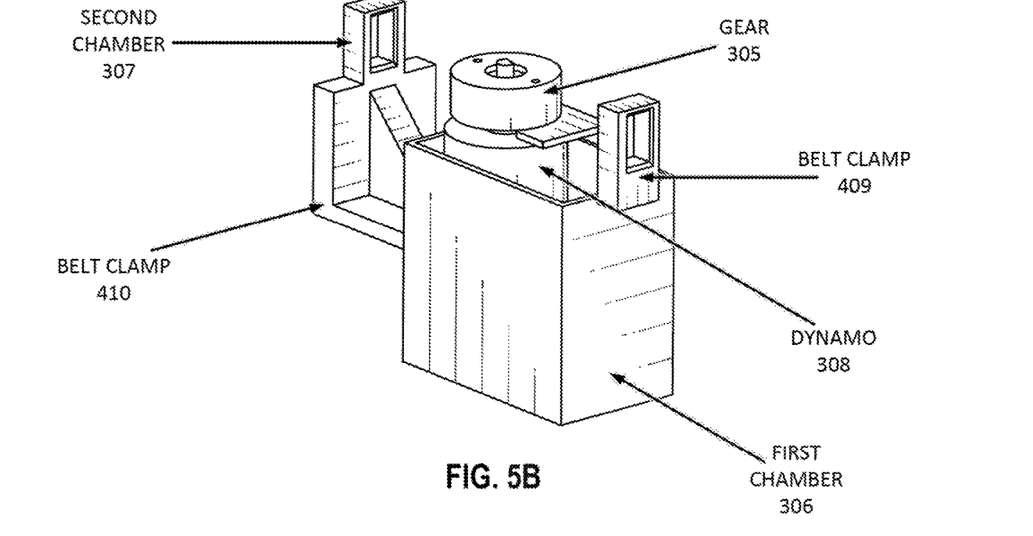
FIG. 5B shows a rendering of the prototype design.

FIG. 5A shows a non-limiting example of a prototype of the present invention. FIG. 5B shows, by way of non-limiting example, a rendering of the prototype design.

In some embodiments, a garment 101 may be disposed on the torso 200 of a user. Non-limiting examples of the garment 101 may include a belt 213 or a harness 214 or a vest. Breathing motions may transversely expand and retract the torso 200, which likewise transversely expand and retract the garment 101. In some embodiments, tension forces from the reciprocating, transverse expansion and retraction of the garment 101 may cause lateral and medial translation of two chambers (306 and 307) of a housing 100. In some embodiments, a spring 303 may be operatively coupled to each chamber such that a spring force 211 is proportional to the reciprocating displacement of the spring 303. In some embodiments, the two chambers (306 and 307) may be configured to slide in one dimension of translational freedom. The chambers may be operatively coupled to a gear 305, such that the reciprocating lateral and medial translation of the chambers rotates the gear 305. The rotation of the gear 305 may drive a dynamo 308 that produces electrical energy.

Figure 4:
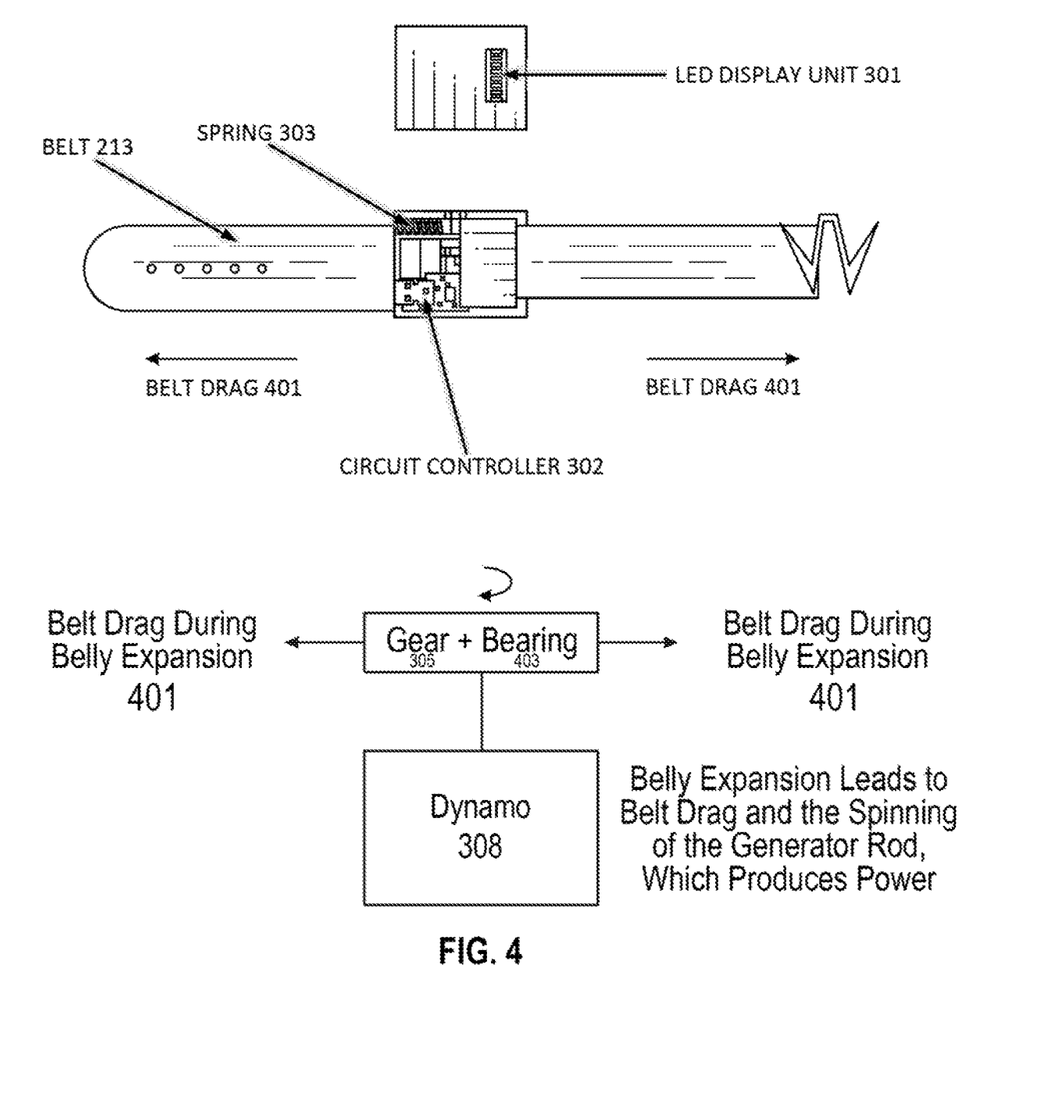
FIG. 4 diagrams the relationship, in some embodiments, between force vectors and the rotation of the gear 306, such that the forces rotate the gear 305, which in turn drives the generator.

FIG. 4 diagrams the relationship, in another embodiment, between belt drag 401 and the rotation of the gear 402 operatively coupled to a bearing 403, such that the forces rotate the gear 402, which in turn drives the generator 404. In some embodiments, the garment 101 is a belt 406. In other embodiments, the garment 101 is a harness 214. In some embodiments, belt clamps (409 and 410) bilaterally disposed on both sides of the device, may secure the device to the garment 101.

In some embodiments, the dynamo 308 may be operatively coupled to a means of storing electrical energy. Non-limiting examples of the energy storage means 207 may include batteries and capacitors. In some embodiments, the energy storage means 207 may be operatively coupled to an electrical output interface 209 having one or more charging means 304 (including such non-limiting examples as USB ports, Firewire ports having 6 pins, HDMI ports, MHL ports, 3.5 mm jacks, etc.) to provide electricity for peripheral devices.

Since reciprocating rotation of the gear 305 would otherwise cause the dynamo 308 to (at times) produce negative voltage, a spinning bearing 403 may be operatively coupled (in some embodiments) to the gear 305 to allow rotation of the gear 305 in only one direction of rotational freedom. In other embodiments, negative voltage may be blocked by a diode 205 that's operatively coupled to the dynamo 308.

In some embodiments, an LED display unit 301 may display a measure of the electrical energy generated by the dynamo 308. In some embodiments, an auxiliary storage means 208 may increase capacity for storing electrical energy. In some embodiments, a circuit controller 302 may provide the stored electrical energy to integrated control functions 212, including (but not limited to) mini-MP3 player, radio, respiration-rate recorder, speakers, Bluetooth interface, GPS interface, voice/sound recorder, emergency notification, and timing or health analyzer (based on the frequency of the reciprocating, breath-associated motion of the torso 200).

Figure 6:
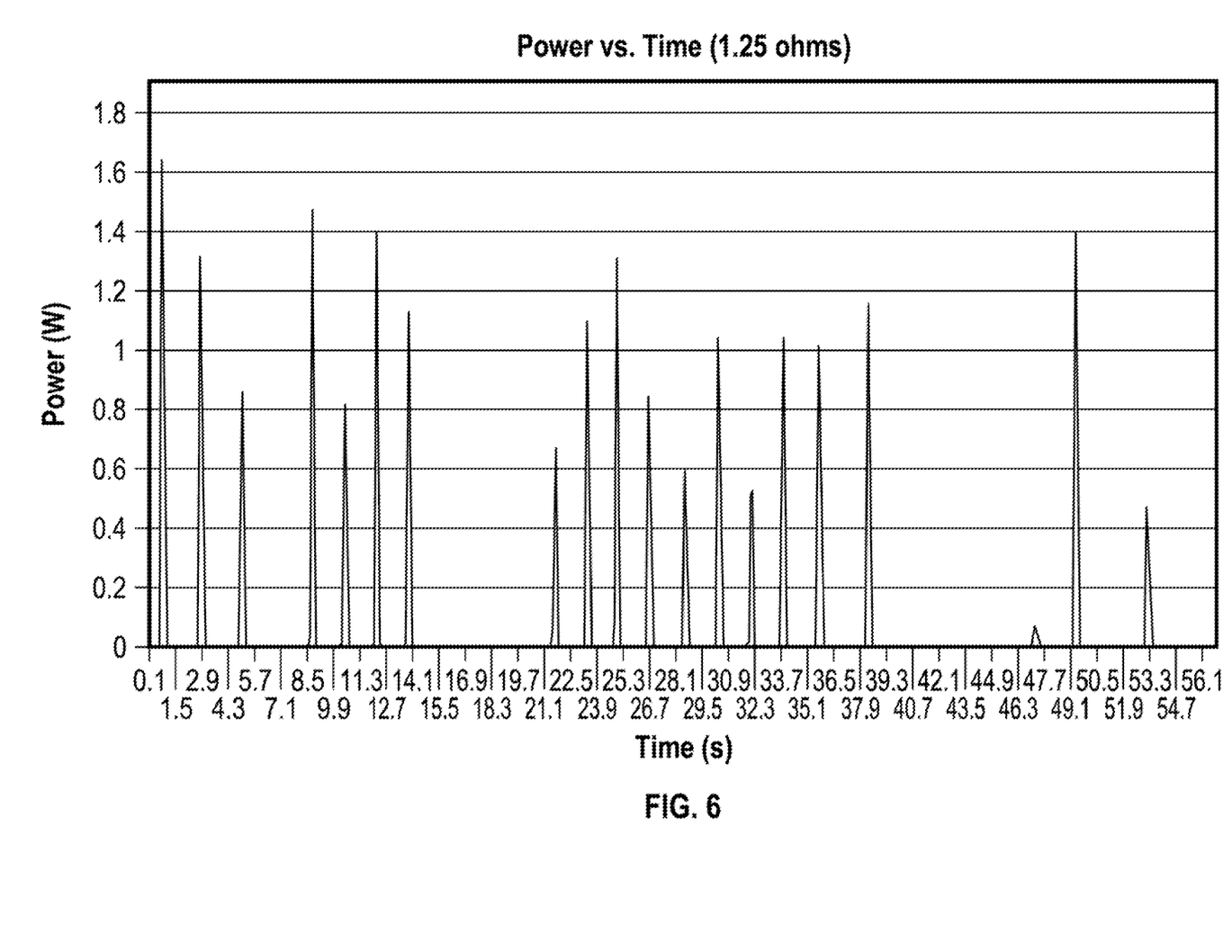
FIG. 6 graphs the present invention's power output over time.

FIG. 6 graphs the present invention's power output over time.

The present invention also provides a method for generating electrical energy using the mechanical energy harnessed from the reciprocating motion associated with breathing. In some embodiments, a user may wear an elastic garment 101. In some embodiments, the garment 101 may be a belt 213. In some embodiments, the garment 101 may be a harness 214. In some embodiments, upon the ventral face of the garment 101, a user may anchor a housing 100 comprising two chambers (306 and 307) (one anchored to a side contralateral to the other) configured to slide in one dimension of translational freedom.

In some embodiments, the user may reciprocate the two chambers (306 and 307) continuously by transversely expanding and retracting the garment 101 via motions associated with breathing. In some embodiments, reciprocating the two chambers (306 and 307) may further involve tension forces translating the chambers medially and laterally, such that the translation rotates a gear 305 coupled to the chambers (306 and 307). In some embodiments reciprocating the two chambers (306 and 307) may further involve a spring force 211 that's proportional to the displacement of a spring that's operatively coupled to each chamber. In some embodiments, reciprocating the two chambers (306 and 307) may further involve the rotating gear 306 driving a dynamo 308, such that the dynamo 308 generates electrical energy.

In some embodiments, reciprocating the two chambers (306 and 307) further involves limiting limit the gear's 305 rotation to only one direction of rotational freedom (in order to prevent negative voltage that would ultimately be produced by the dynamo 308) by coupling the gear 306 to a spinning bearing 403. In other embodiments, reciprocating the two chambers (306 and 307) further involves blocking negative voltage by operatively coupling a diode 206 to the dynamo 308.

In some embodiments, reciprocating the two chambers (306 and 307) may further involve an energy storage means 207 storing the electrical energy generated by the dynamo 308. In some embodiments, the energy storage means 207 may include non-limiting examples such as a battery or a capacitor. In some embodiments, reciprocating the two chambers (306 and 307) may further involve an electrical output interface 209 (e.g. comprising one or more USB ports 304) providing the stored electrical energy to one or more electronic devices via the one or more USB ports 304. In some embodiments, the method of generating electrical energy may involve storing the electrical energy in an auxiliary storage means 208.

In some embodiments, the method of generating electrical energy may involve the user operating a plurality of integrated control functions 212 using a circuit controller 302. In some embodiments, the method of generating electrical energy may involve an LED display unit 301 displaying a measure of the stored electrical energy.

As used herein, the term "about" refers to plus or minus 10% of the referenced number.

Energy storage means 207 (as well as the auxiliary storage means 208) for storing electrical energy may include any such structures known in the art, including (as non-limiting examples) batteries and capacitors. A display may be any device that provides a visual output, including (as non-limiting examples) a computer monitor, a tablet, an LCD screen, an LED screen, one or more diodes configured to express a quantity, etc.

While illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

In some embodiments, the figures presented in this patent application are drawn to scale, including the angles, ratios of dimensions, etc. In other embodiments, the figures are representative only and the claims are not limited by the dimensions of the figures. In some embodiments, descriptions of the inventions described herein using the phrase "comprising" includes embodiments that could be described as "consisting of," and as such the written description requirement for claiming one or more embodiments of the present invention using the phrase "consisting of" is met.

What is claimed is:

1. A method of generating power using mechanical or kinetic energy produced by respiration, comprising
    (a) wearing, by a user, an elastic garment (101), capable of transverse expansion of a torso (200);
    (b) anchoring, by a user, a housing (100) to a ventral face of the garment (101), wherein the housing (100) comprises a first chamber (306) and a second chamber (307), wherein the first chamber (306) is coupled to the second chamber (307) in a configuration that allows the first chamber (306) and the second chamber (307) to slide in one dimension of translational freedom, wherein the first chamber (306) is ventrally anchored to the garment (101) on a first ventral side (201) and the second chamber (307) is ventrally anchored to the garment (101) on a second ventral side (202), wherein the first ventral side (201) and the second ventral side (202) are contralateral to each other, wherein the housing (100) is medial to the first ventral side (201) and the second ventral side (202), wherein a first end of a spring or elastic band (303) is operatively coupled to the first chamber (306) and a second end of the spring or elastic band (303) is operatively coupled to the second chamber (307), (c) reciprocating continuously, by the user, the first chamber (306) and the second chamber (307), comprising:
 (i) expanding transversely the garment (101) by respiration by the user, wherein expanding transversely increases a first tension (203) on the first ventral side (201) and increases a second tension (204) on the second ventral side (202), wherein the first tension (203) and the second tension (204) are inverses,
 (ii) translating laterally each of the first chamber (306) and the second chamber (307) by the first tension (203) and the second tension (204), respectively,
 (iii) rotating, by lateral translation of each of the first chamber (306) and the second chamber (307), a gear (305),
 (iv) driving, by the gear (305), the dynamo (308),
 (v) generating, by the dynamo (308), electrical energy,
 (vi) blocking, by a diode (205), the generated electrical energy if the diode (205) is operatively coupled to the dynamo (308) and a voltage of the generated electrical energy is negative,
 (vii) rectifying, by a rectifier (206), the generated electrical energy,
 (viii) storing, by an energy storage means (207), the generated electrical energy,
 (ix) retracting transversely the garment (101) by respiration of the user, wherein retracting transversely decreases the first tension (203) on the first ventral side (201) and decreases the second tension (204) on the second ventral side (202),
 (x) translating medially each of the first chamber (306) and the second chamber (307) by the first tension (203) and the second tension (204), respectively,
 (xi) rotating, by medial translation of each of the first chamber (306) and the second chamber (307), the gear (305),
 (xii) driving, by the gear (305), the dynamo (308),
 (xiii) generating, by the dynamo (308), electrical energy,
 (xiv) blocking, by the diode (205), the generated electrical energy if the diode (205) is operatively coupled to the dynamo (308) and the voltage of the generated electrical energy is negative,
 (xv) rectifying, by a rectifier (206), the generated electrical energy,
 (xvi) storing, by the energy storage means (207), the rectified electrical energy,
 (xvii) providing, by an electrical output interface (209) comprising one or more charging means (304) operatively coupled to the energy storage means (207), the stored electrical energy to one or more electronic devices via the one or more charging means (304).

2. The method of claim 1 further comprising storing, by an auxiliary storage means (208), the generated electrical energy.

3. The method of claim 1 further comprising:
 (a) operating, by the user, a plurality of control functions (212) using a circuit controller (302); and
 (b) displaying, by an LED display unit (301) operatively coupled to the energy storage means (207), a measure of the stored electrical energy.

4. The method of claim 1, wherein the garment (101) is a belt (213).

5. The method of claim 1, wherein the garment (101) is a harness 214.

6. The method of claim 1, wherein the anchoring of the first chamber (306) is performed by the user attaching a first belt clamp (409) and the second chamber (307) is performed by the user attaching a second belt clamp (410).

7. A portable, respiration-driven, power-generating system comprising:
 (a) an elastic garment (101), capable of transverse expansion of a torso (200);
 (b) a housing (100), comprising:
  (i) a first chamber (306) and a second chamber (307), wherein the first chamber (306) is coupled to the second chamber (307) in a configuration that allows the first chamber (306) and the second chamber (307) to slide in one dimension of translational freedom,
  wherein the first chamber (306) is ventrally anchored to the garment (101) on a first ventral side (201) and the second chamber (307) is ventrally anchored to the garment (101) on a second ventral side (202), wherein the housing (100) is medial to the first ventral side (201) and the second ventral side (202),
  wherein the first chamber (306) and the second chamber (307) are coupled to a spring in a configuration such that
   a medial spring force (211) is proportional to a displacement length of the spring during transverse expansion of the garment (101) and
   a lateral spring force (211) is proportional to a displacement length of the spring during transverse retraction of the garment (101),
  wherein transverse expansion of the garment (101) increases a first tension (203) on the first ventral side (201) and a second tension (204) on the second ventral side (202) and transverse retraction decreases the first tension (203) and the second tension (204), wherein the first tension (203) and the second tension (204) are inverses,
  wherein increasing the first tension (203) and the second tension (204) causes a lateral translation of the first chamber (306) and a lateral translation of the second chamber (307), respectively,
  wherein decreasing the first tension (203) and the second tension (204) causes a medial translation of the first chamber (306) and a medial translation of the second chamber (307), respectively, and
  (ii) a gear (305) operatively coupled to the housing (100) such that a rotation of the gear (305) is caused by a synergy of
   the lateral translation of the first chamber (306) and the second chamber (307) or
   the medial translation of the first chamber (306) and the second chamber (307);
 (c) a dynamo (308) operatively coupled to the gear (305) such that the rotation of the gear (305) produces mechanical or kinetic energy received by the dynamo (308), wherein to prevent negative voltage the dynamo (308) is operatively coupled to a diode (205) and the diode (205) is operatively coupled to a rectifier (206) configured to rectify electrical energy;

(d) the rectifier (206) operatively coupled to an energy storage means for storing the rectified electrical energy;

(e) the energy storage means (207) operatively coupled to an electrical output interface (209) comprising one or more charging means (304), and (f) the electrical output interface (209) configured to provide the stored electrical energy to one or more electronic devices via the one or more charging means (304).

8. The system of claim 7 further comprising:

(a) a circuit controller (302) for a plurality of control functions (212); and (b) an LED display unit (301) for displaying a measure of the generated electrical energy.

9. The system of claim 7, wherein the garment (101) is a belt (213).

10. The system of claim 7, wherein the garment (101) is a harness 214.

11. The system of claim 7, wherein the anchoring of the first chamber (306) is performed by the user attaching a first belt clamp (409) and the second chamber (307) is performed by the user attaching a second belt clamp (410).

* * * * *